United States Patent [19]

Gelbein et al.

[11] 4,277,630

[45] Jul. 7, 1981

[54] CATALYST AND PROCESS FOR PRODUCING AROMATIC HYDROXY COMPOUNDS

[75] Inventors: Abraham P. Gelbein, Plainfield; Ali M. Khonsari, Bloomfield, both of N.J.

[73] Assignee: The Lummus Company, Bloomfield, N.J.

[21] Appl. No.: 15,481

[22] Filed: Feb. 26, 1979

Related U.S. Application Data

[63] Continuation of Ser. No. 853,040, Nov. 21, 1977, abandoned.

[51] Int. Cl.$^3$ .............................................. C07C 37/00
[52] U.S. Cl. ...................... 568/801; 568/802
[58] Field of Search .............................. 568/801, 802

[56] References Cited

U.S. PATENT DOCUMENTS

| Re. 24,848 | 7/1960 | Kaeding et al. | 568/801 |
| 2,727,026 | 12/1955 | Reck et al. | 260/102 |
| 2,727,926 | 12/1955 | Kaeding et al. | 568/801 |
| 2,847,475 | 8/1958 | Voge et al. | 568/801 |
| 2,852,567 | 9/1958 | Barnard et al. | 568/801 |

FOREIGN PATENT DOCUMENTS

| 719287 | 10/1965 | Canada | 568/801 |
| 978918 | 1/1965 | United Kingdom | 568/801 |

OTHER PUBLICATIONS

Kaeding et al., ("Ind. & Eng. Chem."), vol. 53; pp. 805–808 (1961).

*Primary Examiner*—Werren B. Lone
*Attorney, Agent, or Firm*—Louis E. Marn; Elliot M. Olstein

[57] ABSTRACT

A catalyst comprised of oxidized copper, zirconium and an alkali metal is employed for oxidizing an aromatic carboxylic acid to the corresponding phenol; e.g., benzoic acid to phenol.

6 Claims, No Drawings

CATALYST AND PROCESS FOR PRODUCING AROMATIC HYDROXY COMPOUNDS

This is a continuation of application Ser. No. 853,040, filed Nov. 21, 1977 now abandoned.

This invention relates to the production of phenols, and more particularly to the oxidation of aromatic carboxylic acids to phenols and catalyst therefor.

In U.S. Pat. Nos. 2,727,026 and 2,852,567, there are described processes for producing phenols from aromatic carboxylic acids which employ a catalyst including copper oxide. The present invention is directed to an improved process and catalyst for oxidizing an aromatic carboxylic acid to a phenol.

In accordance with one aspect of the present invention there is provided a catalyst of oxidized copper, zirconium and an alkali metal.

In accordance with another aspect of the present invention, there is provided an improved catalytic process for oxidizing an aromatic carboxylic acid having at least one carboxyl group substituted on the aromatic nucleus to the corresponding phenol in which the catalyst is comprised of oxidized copper, zirconium and an alkali metal. The alkali metal is preferably sodium, potassium or lithium.

The catalyst is referred to as being oxidized copper, zirconium and an alkali metal, and such catalyst contains such metals and oxygen. The metals may be present as a mixture of the oxides of copper, zirconium and an alkali metal or as a complex thereof, and such terminology encompasses such mixtures and complexes.

More particularly, the catalyst of the oxidized copper, zirconium and an alkali metal can be employed in the absence or presence of a suitable support material. Thus, for example, the catalyst may be in the form of pellets, extrudates, etc. or supported on a support material, having a surface area of no greater than 50 $m^2/g$; preferably $\alpha$-alumina.

The catalyst includes the three components in an amount effective to catalyze the oxidation of an aromatic carboxylic acid to the corresponding phenol. In general, the catalyst contains the three components in a Cu/Zr/alkali metal atomic ratio in the range of 1/0.05 to 1/0.1 to 5, with the preferred range of 1/0.2 to 0.5/0.5 to 2.5.

The catalyst may be prepared by a variety of procedures known in the art. Thus, for example, the catalyst can be supported on a suitable support by an impregnation or spray drying technique. Alternatively, the three catalyst components can be produced in the form of pellets, extrudates, etc. In preparing a supported catalyst by impregnation, for example, water soluble salts of zirconium and copper, such as the nitrates, are dissolved in water and the solution employed to impregnate a suitable support, such as alpha-alumina.

The impregnated support is dried and calcined to oxidize the copper and zirconium. The resulting catalyst is then treated with an aqueous solution of an alkali metal salt, e.g., the hydroxide, followed by drying and calcination to effect oxidation.

It is to be understood that the above described impregnation technique is only illustrative and this technique and others should be apparent to those skilled in the art.

In accordance with another aspect of the present invention, the hereinabove described catalyst of oxidized copper, zirconium and an alkali metal is employed as the catalyst in the oxidation of an aromatic carboxylic acid to the corresponding phenol. The aromatic carboxylic acid has at least one carboxyl group substituent on the aromatic nucleus, which is generally a benzene or naphthalene nucleus. The aromatic nucleus may also include more than one carboxyl substituent group or may include other substituent groups, such as alkyl, halo, etc. Carboxyl group precursors, i.e., nitrile and amide, may be employed instead of a carboxyl group. The preferred starting materials are the mono carboxylic acids of benzene and alkyl benzenes.

The oxidation is effected with molecular oxygen which can be provided as such or in admixture with other gases; e.g., as air. The oxygen is employed in at least stoichiometric proportions; however, lesser or greater amounts could be employed. In general, oxygen is employed in an amount to provide an oxygen to carboxyl groups mole ratio of from about 0.2:1 to 10:1, and preferably from 0.5:1 to 5:1.

The reaction is generally effected in the vapor phase in the presence of steam as a diluent. The steam also functions to minimize the production of esters that result from the reaction of the carboxylic acid and the product phenol. The steam is generally provided in an amount corresponding to a steam/carboxyl group mole ratio of 5:1 to 500:1 and preferably 10:1 to 100:1.

The oxidation is effected at temperatures of from about 200° to 400° C., and preferably from 250° to 350° C. The oxidation is generally effected at pressures above atmospheric pressure, with the pressure generally being from about 2 to 20 atmospheres.

The catalytic oxidation can be readily effected by the use of any one of a wide variety of vapor-solid contact systems, e.g., employing the catalyst as a fixed or fluidized bed or in a transfer line type of contact system. The above means for effecting the reaction and others should be apparent to those skilled in the art from the present teachings.

The invention will be further described with respect to the following examples; however, the scope of the invention is not to be limited thereby:

EXAMPLE I

Production of Catalyst 12.0 g (0.05 mol) Cu $(NO_3)_2.3H_2O$ and 18.0 g (0.025 mol) ZrO $(NO_3)_2.5H_2O$ were dissolved in 30 g of water and heated to 70°–80° C. The solution was used to impregnate 100 g of a low surface area alpha-alumina (Carborundum SAHT 99, 4–8 mesh). The wet catalyst was dried and calcined at 750° C. for two hours, during which time the nitrates decomposed to their corresponding oxides. This catalyst (100 g) was treated with a solution of 4.3 g (0.077 mol) KOH in 30 g of water. The resulting catalyst was dried and calcined at 500° C. for approximately 16 hours. The finished catalyst had the following composition (wt.%): 4.0% CuO, 3.0% ZrO, 3.6% $K_2O$ remainder alumina.

EXAMPLE II

The activity and selectivity of the catalyst in Example I for producing phenol from benzoic acid were measured in a fixed bed reactor. The reactor was a jacketed 1'×1" dia. 316 stainless steel tube. Boiling Dowtherm was used in the jacket for temperature control. The feed was prepared by metering water through a heater at reactor pressure, passing the steam so produced through a benzoic acid saturator maintained at a temperature required to give the desired benzoic acid/water ratio, and then mixing the stream with the desired amount of air. The reactor contained 60 g of catalyst. Operating conditions and results are given in Table I.

TABLE I

| Temp., °C. | Press., psig | Run Time, hrs. | Feed Composition (mole ratio) | | | Space Velocity GHSV (STP), hr$^{-1}$ | Conversion, % | Space Yield, g/g cat/hr. | Selectivities, mole % | | |
|---|---|---|---|---|---|---|---|---|---|---|---|
| | | | COOH | H$_2$O | O$_2$ (air) | | | | Benzene | Phenol | Diphenyl oxide |
| 280–310 | 90–100 | 3.0 | 1 | 38 | 0.6 | 2630 | 35.1 | 0.0816 | 2.3 | 76.1 | 5.4 |
| 280–310 | 120 | 3.0 | 1 | 74 | 1.5 | 2200 | 63.7 | 0.0487 | 2.0 | 69.1 | 2.7 |
| 300–305 | 105 | 2.5 | 1 | 33 | 1.2 | 2600 | 32.6 | 0.0725 | 4.0 | 82.2 | — |

The present invention is particularly advantageous in that it provides for improved selectivity. In addition, it provides a more economic method for converting aromatic carboxylic acids to phenols. This advantage derives from:

(1) Lower cost reactor system (vapor phase reactor vs. liquid phase molten salt reactor).

(2) Elimination of a difficult to dispose of waste stream. The conventional process must draw off a slip stream from the molten mass to maintain catalyst activity. This slip stream contains heavy metals and organics which cannot be simply incinerated for disposal.

(3) Waste heat recovery. The reaction is highly exothermic. The vapor phase reaction is conducted in a temperature range approximately 100° C. higher than the liquid phase reaction, making it possible to recover the heat of reaction (e.g., as high pressure steam) at a more efficient temperature level.

(4) The potential for higher yields when producing alkylsubstituted phenols (e.g., cresols). These are less volatile than phenol and, therefore, are more difficult to strip out of a liquid phase. It is well known that if the phenols are not removed from the liquid phase, they will further react and ultimately produce tars.

Numerous modifications and variations of the present invention are possible in light of the above teachings and, therefore, within the scope of the appended claims the invention may be practiced otherwise than as particularly described.

We claim:

1. A process for catalytically oxidizing an aromatic carboxylic acid selected from the group consisting of benzoic acid and alkyl substituted benzoic acid to the corresponding phenol at improved selectivity, comprising:

contacting said aromatic carboxylic acid with oxygen and steam in the presence of a catalyst at a temperature of from 200° C. to 400° C. and at a pressure of from 2 to 20 atmospheres, with an oxygen to carboxyl group mole ratio of from 0.2:1 to 10:1, and a steam to carboxyl group mole ratio of from 5:1 to 500:1, said catalyst being comprised of oxidized copper, zirconium and an alkali metal wherein the copper:zirconium:alkali metal atomic ratio is from 1:0.2 to 0.5:0.5 to 2.5.

2. The process of claim 1 wherein the oxidized copper, zirconium and alkali metal is supported on a support having a surface area of no greater than 50 m$^2$/g.

3. The process of claim 2 wherein the support is α-alumina.

4. The process of claim 3 wherein the alkali metal is potassium.

5. The process of claim 3 wherein the alkali metal is lithium.

6. The process of claim 3 wherein the alkali metal is sodium.

* * * * *